United States Patent [19]

Ueno

[11] Patent Number: 4,553,935

[45] Date of Patent: Nov. 19, 1985

[54] APPARATUS FOR WAXING-UP

[75] Inventor: Masato Ueno, Hiroshima, Japan

[73] Assignee: Kyocera Corporation, Japan

[21] Appl. No.: 566,174

[22] Filed: Dec. 20, 1983

[51] Int. Cl.4 ............................................. A61C 3/00
[52] U.S. Cl. .................................... 433/32; 222/146.5
[58] Field of Search ...................... 433/32; 222/146 H

[56] References Cited

U.S. PATENT DOCUMENTS

| | | | |
|---|---|---|---|
| 1,092,307 | 4/1914 | Talbott et al. ........................ | 433/32 |
| 2,086,462 | 7/1937 | Bost ....................................... | 433/32 |
| 4,150,770 | 4/1979 | Wieland et al. .............. | 222/146 HE |

Primary Examiner—Robert Peshock

Attorney, Agent, or Firm—Spensley Horn Jubas & Lubitz

[57] ABSTRACT

The present invention primarily relates to an apparatus for improving the efficiency of the waxing-up work mainly in the dental technology. The apparatus comprises a casing which can be held in the palm of the operator's hand, a nozzle member connected to the end of the casing, a means for heating and a means for feeding bar-shaped solid wax which is accommodated in the casing. This apparatus allows the operator to ooze out a proper amount of melted wax required for the waxing-up work from the end of the nozzle member and can solve many problems caused by the conventional method using spatulas.

16 Claims, 14 Drawing Figures

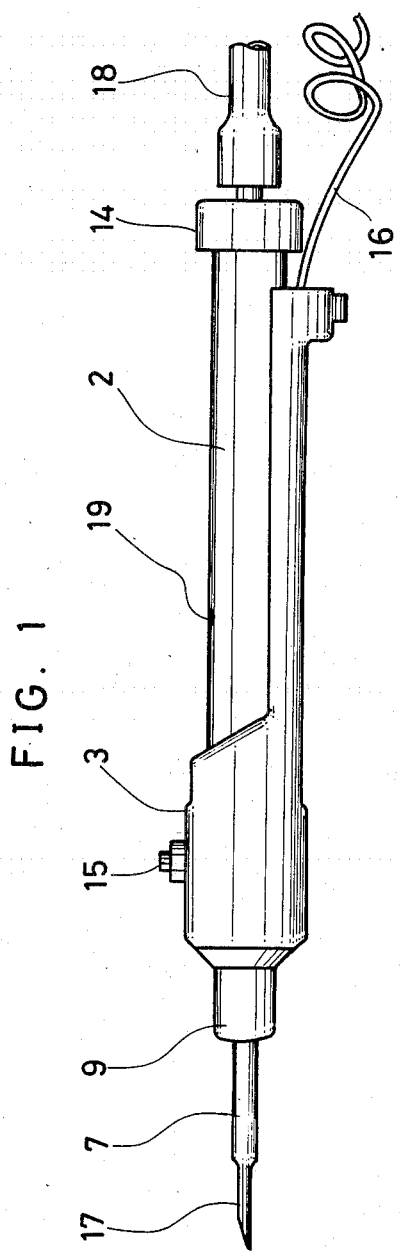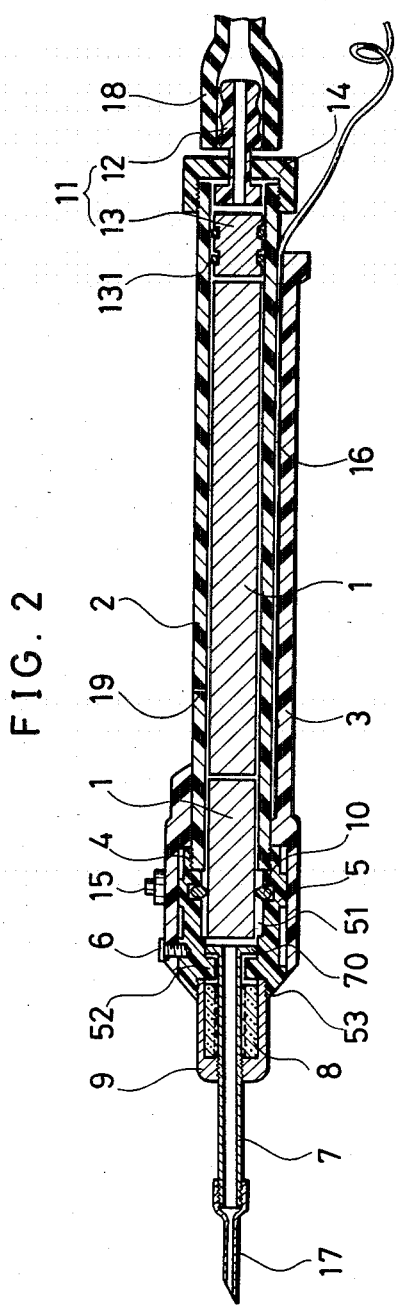

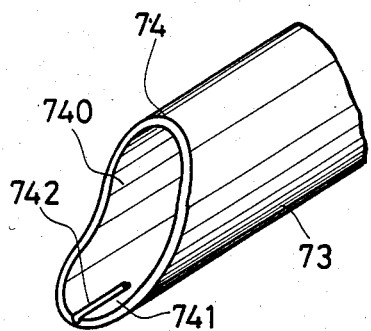 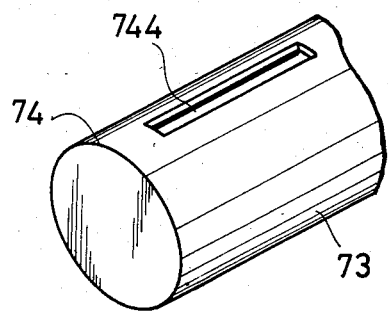
FIG.10A  FIG.10B
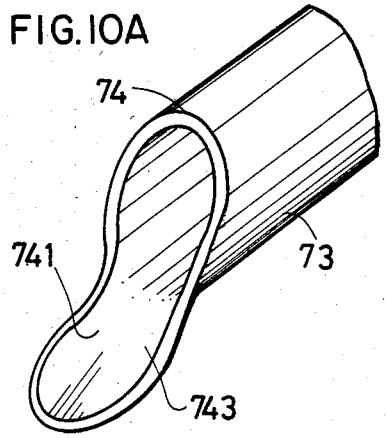 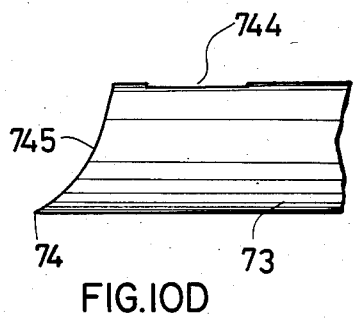
FIG.10C  FIG.10D
FIG. 11
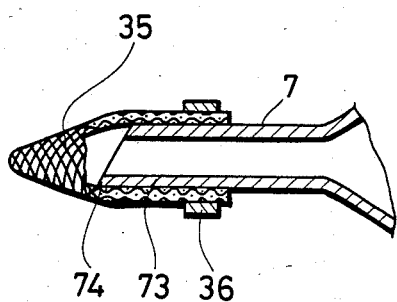

APPARATUS FOR WAXING-UP

BACKGROUND OF THE INVENTION

1. Field of the Invention

This invention relates to an apparatus for waxing-up, which is used to mainly melt dental wax and to perform waxing-up work (what is called "waxing-up method"). Dental waxing-up method is taken as an example in the following description.

2. Prior Art

Dipping, cone forming and rising line forming have been the conventional procedures for the waxing-up method to make tooth molds in the dental field. In these procedures, a dental technician scoops melted wax in the melting pot using a wax spatula, or he scoops solid wax using a heated spatula, reheats the wax with a gas burner and builds up the wax over a model abutment.

In this conventional waxing-up method, the wax may be overheated while reheated by the gas burner, resulting in deterioration of the wax material. In addition, since the wax is heated and melted in the melting pot by an electric heater or gas burner for a long time during the waxing-up work, various additives in the wax are separated and precipitated at the bottom of the pot. As a result, the wax itself is deteriorated, and the usable amount of wax is reduced since the precipitated substances cannot be used for the waxing-up work.

Furthermore, the above-mentioned conventional method requires extremely frequent reciprocating motions. When building up the wax over the crown of the first molar tooth, for example, 30 to 50 times of reciprocating motions are required between the pot (burner) and the mold abutment. This takes a long work time. To make matters worse, when the wax, made of oil, is melted, substances harmful to human body are generated and fumes from the melted wax are also harmful to human body. These harmful substances and fumes are greatly generated especially from the wax pot, since a great amount of wax is melted at a time. When the conventional method is used, these harmful substances and fumes have been unavoidable. These problems have indicated an obvious need for waxing-up work unharmful to operators.

SUMMARY OF THE INVENTION

It is therefore the principal object of the present invention to provide an apparatus allowing use of a waxing up method wherein only the minimum amount of wax is melted and the melting temperature is maintained at a proper level to prevent the wax from being deteriorated. The present invention provides an apparatus which can deliver a required amount of melted wax from the nozzle member connected to the front end of a casing which can be held in the palm of the operator's hand. The front end of the nozzle member can have a configuration suited for waxing-up work, and an adaptor can be used for the nozzle member to meet various waxing-up work requirements. Bar-shaped solid wax is used. Before a solid wax bar is consumed, another bar is supplied from the rear or front of the casing. In a preferred embodiment of the present invention, wax bars are fed pneumatically or manually. The feed amount is properly controlled to supply a required amount of wax. Since the apparatus of the present invention melts solid wax in the closed casing and the nozzle member, environments are maintained clean and wax can be melted promptly. Thus the apparatus of the present invention can solve all problems of the prior art.

Other advantages and the details of the present invention will become more apparent when preferred embodiments of the present invention are considered in connection with the drawings.

BRIEF DESCRIPTION OF THE DRAWINGS

FIG. 1 is a side view of the first embodiment of the present invention;

FIG. 2 is a vertical sectional side view of the first embodiment;

FIGS. 10 (A), (B), (C) and (D) indicate various shapes of the front end of the nozzle member; and FIG. 11 is a partial cutaway vertical sectional side view indicating a wax exuding adaptor attached to the front end of the nozzle member.

DETAILED DESCRIPTION OF THE PREFERRED EMBODIMENTS

Figure 3:
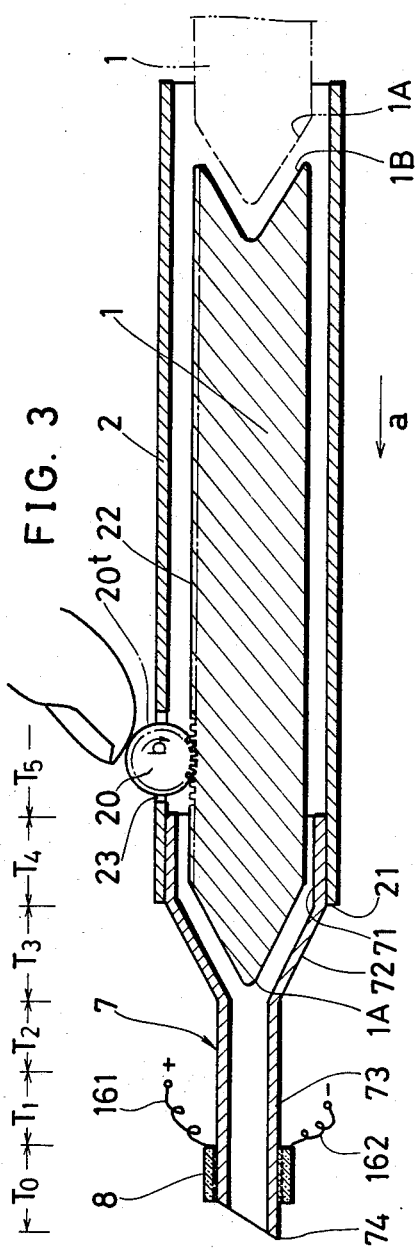
FIG. 3 is a vertical sectional side view of the second embodiment.

The following embodiments include the first embodiment wherein the means for feeding wax is operated pneumatically, the second embodiment wherein the feed gear for the means for feeding wax is driven by finger operation, the third embodiment which is a developed embodiment of the heating means of the second embodiment, modified and developed embodiments of the means for feeding wax of the second and third embodiments, and modified embodiments regarding the front end shape of the nozzle member and the construction of the adaptor.

First of all, the first embodiment is described in detail. Referring to FIGS. 1 and 2, a casing 2 which accommodates a cylindrical dental solid wax 1 is composed of a heat-resistant material such as a heat-resistant plastic material. The casing 2 is fit and supported along its entire length by a retaining sleeve 3 made of a heat-resistant material. The front side of the retaining sleeve 3 is cylindrical and the rear side is almost semi-cylindrical. A hollow connection member 5 made of a heat-resistant plastic material is removably connected at the front end of the casing 2 via a screw 4. The cylindrical retaining sleeve 3 enclosing the connection member 5 is fixed on the connection member 5 by a set screw 6 in the radial direction. A nozzle member 7 made of a copper or a material which is superior in heat conductivity and a means for heating wax 8 are securely connected at the front end of the connection member 5. To assemble the nozzle member 7 and the means for heating wax 8, the nozzle member 7 having a flange-shaped heating plate 70 at its rear end is inserted from the hollow portion 51, and the cylindrical heating element 8 is coaxially fit on the nozzle member 7, and the means for heating wax 8 is enclosed by a heater cover 9 made of a heat-resistant material, and the cover 9 is screwed in a screw 53 at the front end of the connection member 5 so that the flange-shaped heating plate 70 located at the rear end of the nozzle member 7 contacts the front wall 52 of the hollow portion 51 of the connection member 5 so that the nozzle member 7 cannot be extracted forward. In this way, the nozzle member 7 and the means for heating 8 are removably connected respectively to the connection member 5.

The means for heating wax 8 is a cylindrical ceramic heater wherein a heating element is provided by evaporating an electrical resistor material on a cylindrical ceramic body, and is hermetically covered with ceramic material for insulation.

A seal ring 10 is provided between the rear side of the hollow portion 51 of the connection member 5 and the external circumference of the solid wax 1 to store melted wax in the hollow portion 51 and to prevent the melted wax from flowing in the reverse direction. A means for feeding wax 11 includes a compressed air inlet member 12 connected to the rear end of the casing 2 and a plunger 13 movably accommodated in the casing 2. A joiner 14 is screwed at the rear end of the casing 2 to airtightly connect the inlet member 12 to the rear end of the casing 2. The plunger 13 has an air-tight seal ring 131. The inlet member 12 is connected to a means for supplying compressed air through an air hose 18. A switch 15 is provided on the retaining sleeve 3 to supply and shut off compressed air. The numeral 16 designates a power supply lead which is passed through between the casing 2 and the semi-cylindrical retaining sleeve 3 and is branched to the switch 15 and the means for heating wax 8. An ON/OFF switch outside the apparatus controls power supply to the means for heating wax 8. At the front end of the nozzle member 7, a hollow needle-shaped adaptor 17 is removably connected via a screw. The length of the casing 2 is sufficiently longer than the solid wax bar 1 so that a new wax bar can be supplied from the rear when the wax 1 is melted and shortened. Regarding replenishment of wax, an air exhaust aperture 19 is provided close to the front end of the casing 2. When the plunger 13 advances beyond the air exhaust aperture 19, the air supplied from the inlet member 12 is discharged externally through the air exhaust aperture 19. An exhaustion sound generated at this time notifies the operator that the wax in the casing 2 has been consumed so that a new wax bar can be properly replenished.

The operation procedure and functions of the first embodiment are described below.

First, supply the bar-shaped solid wax for dental use in the casing 2. Hold and move the casing 2 forward while sliding it along the internal surface of the sleeve 3, and connect it to the screw 4 of the connection member 5. Activate the means for supplying air using the switch 15 to supply air in the casing 2 through the air inlet member 12. Thus the plunger 13 is pushed and the front end of the wax 1 contacts the heating plate 70 in the connection member 5. Simultaneously, the ceramic heater 8 is powered using an external switch and heated to heat the nozzle member 7 which passes through the inside of the heater 8. The inside of the connection member 5 should be heated up to 100°-120° C. for example so that the wax 1 in the connection member 5 can be melted sufficiently. The heat from the heated nozzle member 7 is conducted to the heating plate 70, and the front side of wax 1 contacting the heating plate 70 is melted and liquified. The melted wax is fed from the heating plate 70 into the nozzle member 7 by the pressure of the plunger 13. Then the melted wax passes through the nozzle member 7, is oozed from the needle-shaped adaptor 17 and is used for waxing-up work. When the wax 1 in the casing 2 has been consumed after continuous waxing-up work, the plunger 13 moves forward beyond the air exhaust aperture 19 in the casing 2, and an air exhaust sound is generated from the air exhaust aperture 19. At this time, turn off the switch 15 and the power to the ceramic heater 8. Remove the casing 2 from the screw 4 of the connection member 5, and push in a new solid wax 1 from the front end of the casing 2. Then connect the front end of the casing 2 to the screw 4 of the connection member 5. This completes wax replenishment and the next waxing-up work is ready.

For the maintenance work of this apparatus, the nozzle member 7 should be removed from the connection member 5 as described below. First, remove the heater cover 9 screwed on the connection member 5 and remove the wax inside the connection member 5. Then press the nozzle member 7 to the casing 2. The nozzle member 7 can now be removed from the hollow portion 51 of the connection member 5. The adaptor 17 can easily be removed since it screwed on the nozzle member 7. Therefore, it can easily be replaced with other needle-shaped adaptors with various needle diameters and tip configurations. The first embodiment offers the following advantages since it has the above-mentioned construction and functions.

(i) The efficiency of waxing-up work can be improved since the melted wax suited for waxing-up work is continuously supplied from the front end of the nozzle member 7.

(ii) The casing 2 is removable from the connection member 5 for easy wax replenishment and maintenance of the apparatus.

(iii) Since the heater 8, the nozzle member 7 and the connection member 5 are removable from one another, the heater 8 and the nozzle member 7 can be selectably replaced as desired according to application. The adaptor 17 is also removable and selectably replaced. Therefore, the maintenance and assembly of the apparatus are easy.

(iv) Melted wax can be supplied at all times even when the wax 1 is melted continually. This reduces power consumption to a relatively low level.

Next, the second embodiment and its modified embodiments are described. The second embodiment includes a means for manually feeding solid wax by finger actions. The identical numerals are assigned to the members identical to those of the first embodiment. Referring to FIG. 3, the casing 2 is a hollow cylinder. Its rear end is open. The nozzle member 7 is fit and secured in the front end of the casing 2. The nozzle member 7 includes a large-diameter open rear end 71, a small-diameter pipe-shaped front end 73 with an oblique cutting angle at its tip and a forwardly throttled midway portion 72. The rear end 71 of the nozzle member 7 is pressure-fit in the front end 21 of the casing 2. Thus the nozzle member 7 is integrated with the casing 2. The means for heating wax 8 is a ceramic heater wound around the front end 73 of the nozzle member 7. The construction of the heater 8 is identical to that of the first embodiment. The numerals 161 and 162 designates power supply leads to the ceramic heater 8. The means for supplying power to the heater is provided outside the drawing. The front end 1A of the dental wax 1 has a cone shape which has a taper identical to that of the throttled midway portion 72 of the nozzle member 7. The rear end 1B of the wax 1 is recessed so that it closely fits the cone-shaped front end 1A of another wax 1 to be supplied next. Moreover, rack grooves 22 with a constant width are provided on the upper circumferential surface of the wax 1 at a constant pitch in the longitudinal direction.

The numeral 20 designates a main feed gear rotatably supported in a window hole 23 provided in the casing 2. The external teeth 20t of the gear 20 engage with the rack grooves 22. The means for coaxially supporting the wax 1 in the casing 2 and the means for supporting the main feed gear 20 are not shown in the drawing for simplification.

The operation and functions of the second embodiment with the above-mentioned construction are described below. To operate this apparatus, first, turn on the power supply connected to the leads 161 and 162. The power is supplied to the ceramic heater 8 and the heater is heated. By continuously supplying power to this ceramic heater 8, the nozzle member 7 is continuously heated, heat is conducted from the front end 73 to the rear end 71 of the nozzle member 7, and the hollow portion of the nozzle member 7 is heated. Since the nozzle member 7 itself radiates heat and the rear end 71 has a large diameter, the temperature of the hollow portion of the nozzle member 7 has a temperature gradient, that is, the temperature is lower at the place closer to the rear end.

More specifically, the temperature gradient is represented by $T_0$ $T_1$ $T_2$ $T_3$ $T_4$ $T_5$ where $T_0$ is the temperature at the hollow portion close to the tip 74 of the nozzle member 7, $T_1$ and $T_2$ are the temperatures at the front end 73 of the hollow portion, $T_3$ is the temperature at the throttled midway portion 72 of the hollow portion, $T_4$ is the temperature at the rear end of the hollow portion, and $T_5$ (room temperature) is the temperature outside the nozzle member 7 and inside the hollow portion of the casing 2. According to our experiment, the proper temperature for the conventional dental wax are $T_0=100°$ C., $T_1=80°$ C., $T_2=60°$ C., $T_3=40°$ C., $T_4=30°$ C. and $T_5=20°$ C. The construction of the ceramic heater 8 and the material and configuration of the nozzle member 7 have been carefully considered to obtain such temperature gradient.

Next, insert the cone-shaped end 1A of the solid wax 1 into the rear open end of the casing 2 in the direction of the arrow a, and engage the rack grooves 22 of the wax 1 with the external teeth 20t of the main feed gear 20. Rotate the main feed gear 20 in the direction of the arrow b using a finger to further move the wax 1 in the direction of the arrow a and to closely contact the front end 1A of the wax 1 to the inner wall of the throttled midway portion 72 of the nozzle member 7. The front end 1A of the wax 1 is softened by the heat from the hollow portion which is heated at the temperature $T_3$ and by directly depriving heat from the nozzle member 7. Although the solid wax 1 has a larger diameter than that of the front end 73 of the nozzle member 7, after it is heated and softened, it is deformed and can be forcibly fed into the hollow portion of the end 73 of the nozzle member 7. When the main feed gear 20 is further rotated in the direction of the arrow b, the softened end of the wax 1 is further forcibly moved to the front end 73 and the tip 74 of the nozzle member 7. Since the temperatures $T_1$ and $T_0$ at the front end 73 and the tip 74 are higher than the melting point of the dental wax 1, the softened end of the wax 1 is melted. As a result, the melted wax is accumulated at the tip 74 and the front end 73 of the nozzle member 7 and is kept warm at constant temperature of $T_0$ and $T_1$. Since the softened part of the solid wax closely contacts the inner wall of the throttled midway portion 72 of the nozzle member 7, the melted wax will not leak even when the nozzle member 7 is directed upward.

The melted wax obtained in this way is brought to the desired mold abutment (not shown) to allow waxing-up work. At this time, this apparatus should be located close to the mold abutment. Rotate the main feed gear 20 using a finger to obtain a proper amount of melted wax whenever melted wax is required. Like the first embodiment, the second embodiment also enables waxing-up work to be performed extremely quickly, resulting in drastic work time reduction. Waxing-up work is also made extremely easier. In addition, since only the required amount of wax is melted at the required time, harmful substances generated while melting the wax and fumes generated from the melted wax are minimal, thus harmful effects to human body are extremely reduced. Accordingly, the total electric power required for melting the wax can also be reduced.

Figure 4:
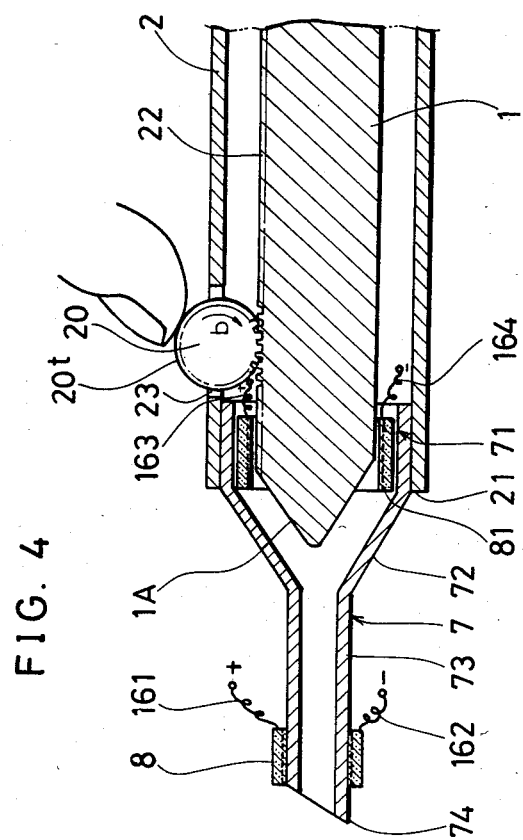
FIG. 4 is a vertical sectional side view of the main section of the third embodiment.

FIG. 4 shows another embodiment of the present invention. Unlike FIG. 3, a cylindrical ceramic heater 81 is provided inside the rear end 72 of the nozzle member 7, and the power is supplied through the leads 163 and 164 of the heater. The heater 81 can be powered by a power supply (not shown) different from the power supply for the ceramic heater 8. Or both heaters 81 and 8 can be connected in series. The construction of this newly provided heater 81 is similar to that of the heater 8. The heating capacity and configurations of the heater 81 have been designed to maintain the proper temperature required for softening the solid wax 1 in the casing 2.

Even in the embodiment with the newly equipped ceramic heater 81, the front end 1A of the wax 1 is softened mainly by the heater 81 and melted in the nozzle member 7 by the ceramic heater 8. The melted wax is used for waxing-up work as described before. Conventional heaters such as a nichrome wire can also be used to heat the solid wax 1. However, the ceramic heater has advantages in light weight, compact size and long service life. The position, quantity and construction of the heater as a means for heating wax are not limited by the embodiment. The point of the present invention is the formation of a proper temperature gradient required for softening and melting the solid wax in the moving direction of the wax. An example of the heater which can provide such temperature gradient is a ceramic heater in which a heating element is arranged so that its density is high at the external surface of the tip 74 of the nozzle member 7 and is reduced as extended to the rear end 71. A nichrome wire can also be used by arranging its winding density as described above. The melting temperature and the retaining temperature suited for waxing-up work vary according to the type of dental solid wax. To meet these temperature conditions, the heater can be modified. However, it is more convenient to change the voltage of the separately provided power supply or to control the power by adjusting the current flowing in the heater using a variable resistor.

The softening and melting temperature may become excessive if the wax is overheated by the heater. To solve this problem, a thermostat should be provided in the hollow portion of the nozzle member 7 to shut off power to the heater.

Figure 5:
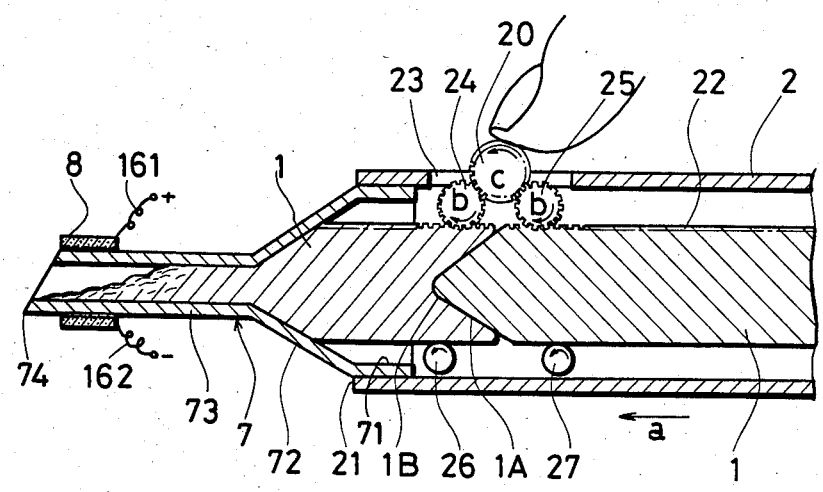
FIG. 5 is a vertical sectional side view of the main section of the second embodiment, indicating a modified means for feeding wax.

FIG. 5 shows a developed embodiment of the wax feeding means of the second embodiment.

A pair of driven feed gears 24 and 25, and the main feed gear 20 which engages with the external teeth of both the driven feed gears 24 and 25 are provided in the window hole 23 in the casing 2. Idler rollers 26 and 27 are provided opposite to the feed gears 24 and 25 across the wax 1. The dental wax is held and fed by the driven feed gears 24 and 25 engaging with the rack grooves 22 of the wax 1 and the idler rollers 26 and 27.

When the main feed gear 20 is rotated in the direction of the arrow c (forward) using a finger, the pair of driven feed gears 24 and 25 are rotated in the direction of the arrow b. Thus the wax 1 is fed in the direction of the arrow a (forward).

When the wax fed by this means for feeding has nearly consumed, the wax 1 are held only by the driven feed gear 24 and the idler roller 26. The front part of the second wax 1 is held by the other driven feed gear 25 and the idler roller 27. Therefore, both the first wax 1 and the subsequent second wax 1 are all held by these gears and rollers, thus the second wax 1 is prevented from being drifted away from the casing 2.

Figure 6:
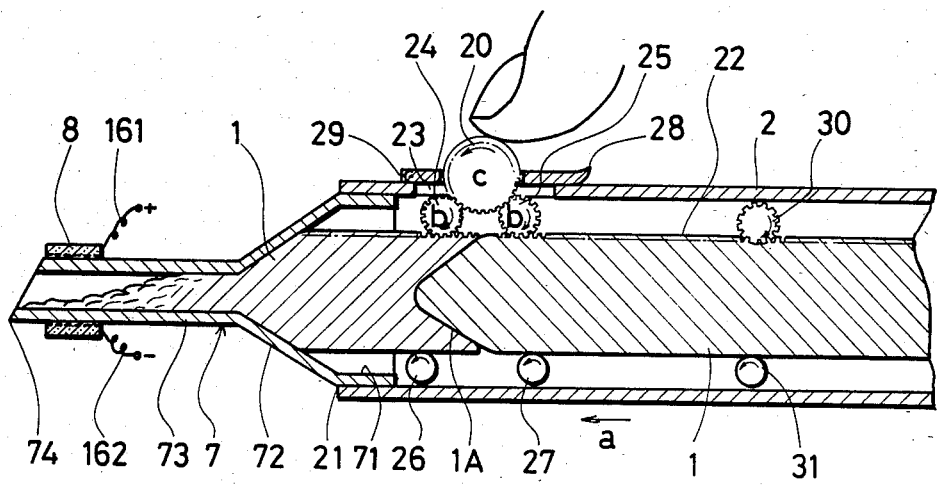
FIG. 6 is a vertical sectional side view of the main section of the second embodiment, indicating another modified means for feeding wax.
Figure 7:
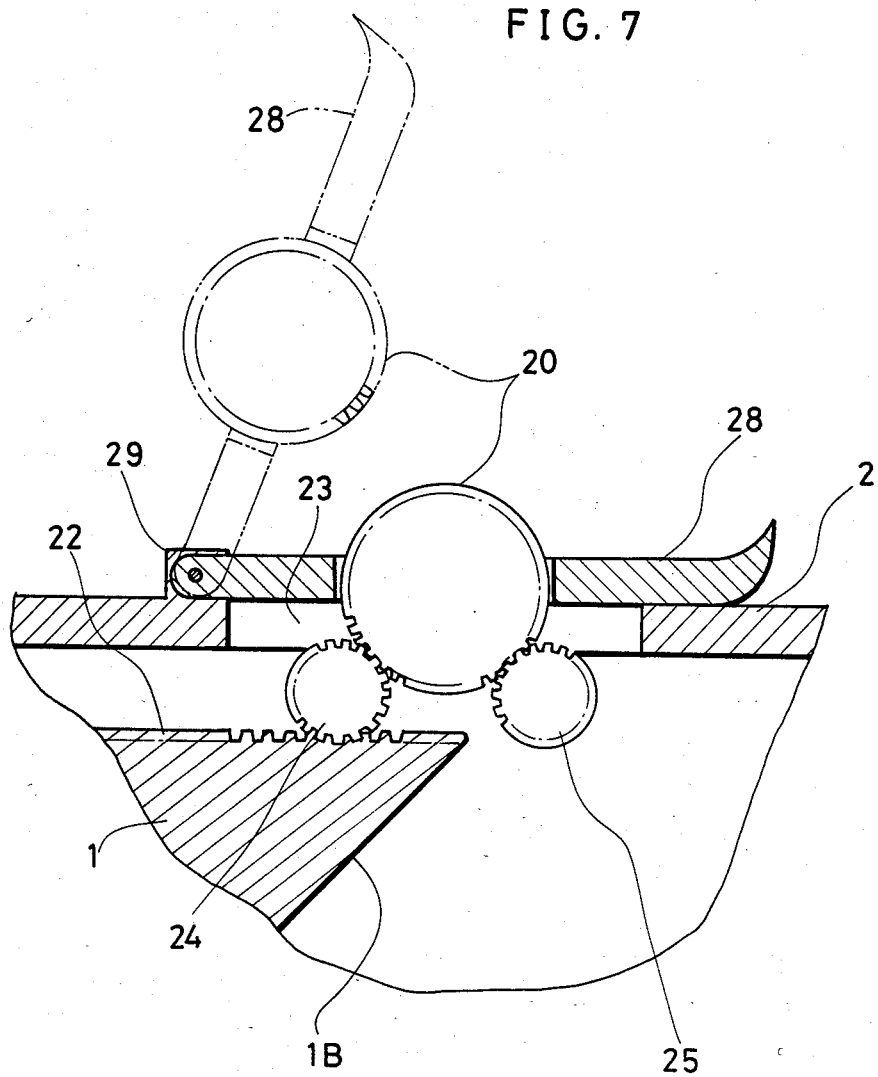
FIG. 7 is an enlarged sectional side view of the main section of FIG. 6.

FIGS. 6 and 7 show another embodiment of the means for feeding wax. This embodiment has a construction to further smoothen the insertion of the subsequent wax. Unlike the embodiment shown in FIG. 5, the main feed gear 20, which is rotated using a finger to feed the wax 1, 1, is rotatably installed to a lever 28, and the one end of the lever 28 is pivotally connected to the projection 29 of the casing 2. Both the driven feed gears 24 and 25 are rotatably installed to the casing 2 in the same way as the previous embodiment. When the lever 28 is pressed against the casing 2 and secured, the main feed gear 20 installed to the lever 28 engages with both the driven feed gears 24 and 25. Therefore, the wax 1, 1 can be held and fed in the same way as described for the embodiment shown in FIG. 5.

When the first wax 1 is nearly consumed, and its rear end is held only by the driven feed gear 24 and the idler roller 26, the lever 28 is lifted as shown by the broken lines in FIG. 7. Thus the main feed gear 20 is disengaged from the driven feed gear 25 to free the driven feed gear 25. At this time, the driven feed gear 30 installed to the casing 2 to stabilize the wax 1 and both idler rollers 26 and 31 are also free to rotate. Insert the second wax 1 between the driven feed gear 30 and the idler roller 31 which are provided opposite to each other and between the driven feed gear 25 and the idler roller 27 which are also provided opposite to each other. Push the wax 1 until the cone-shaped front end 1A fits the recessed rear end 1B of the first wax 1. Then lower the lever 28 to the position indicated by the solid lines to engage the main feed gear 20 with the driven feed gears 24 and 25 at the same time. Accordingly, the second wax 1 held by the driven feed gear 25 and the idler roller 27 can be fed by the rotation of the main feed gear 20 as described above.

Figure 8:
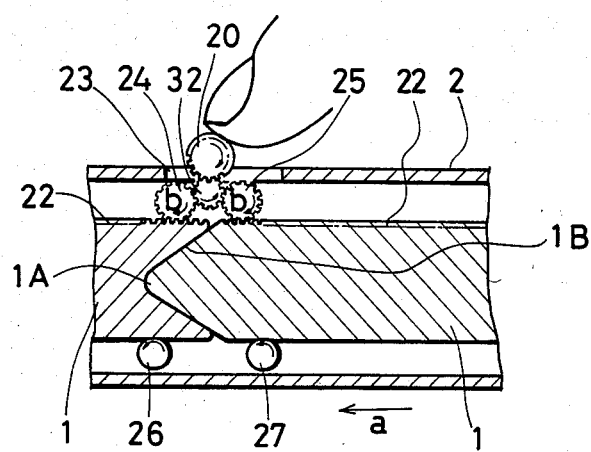
FIG. 8 is a vertical sectional side view of the main section of the second embodiment, indicating the third modified means for feeding wax.

It is usually difficult to rotate the gear 20 by pushing it (in the direction of the arrow c) using a finger in the above embodiments. It is preferable to rotate the gear 20 by pulling it using an additional intermediate gear 32 engaging with the main feed gear 20 and the driven feed gears 24 and 25 as shown in FIG. 8.

When the rack grooves 22 are not provided on the dental wax 1, 1, the circumferences or the entire structures of the driven feed gears 24 and 25 can be made of rubber so that the elastic deformation of the rubber together with the idler rollers 26 and 27 can securely hold the wax 1 at the upper and lower positions. In this case, the main feed gear 20 for providing a rotating force to the driven feed gears should be installed so that the external teeth of the gear 20 deeply engage with the mating driven feed gears.

Figure 9:
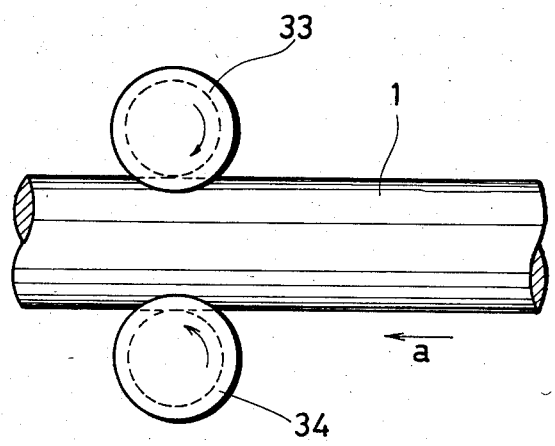
FIG. 9 is a schematic view of a means for feeding wax using rollers instead of gears.

In the embodiment shown in FIG. 9, the wax 1 does not have any rack grooves 22 but is a simple round bar. In this case, a pair of upper and lower rubber drum rollers 33 and 34 are provided in the casing 2 as an example means for feeding the wax. The wax 1 can be fed by a friction force when the bar wax 1 is held between the rollers 33 and 34, and the rollers are rotated directly or indirectly using a finger. In this case, the shapes of the front end 1A and the rear end 1B are identical to those shown in FIGS. 3 to 8.

The second and third embodiments, and developed and modified embodiments regarding the means for feeding have been described.

Referring to FIGS. 10(A)–10(D), various embodiments of the front end of the nozzle member are described. The tip 74 shown in FIG. 10(A) comprises an opening 740 made by cutting the cylinder obliquely and a reservoir 741 which is provided by gradually reducing the slope of the lower portion of the opening and by expanding the opening. A guide groove 742 with a constant depth is provided at the approximately central position of the reservoir 741 in the longitudinal direction. The nozzle member has been designed to deliver melted wax along this guide groove 742 so that the nozzle member is suited for waxing-up work requiring a minute amount of wax.

The guide groove 742 can be modified to slits with a constant interval. Referring to FIG. 10(B), a spatula tip 743, which has the same shape as the wax scooping portion of the conventional wax spatula, is provided at the lower portion of the reservoir 741. Using this spartula-shaped tip, the operator who is accustomed to the conventional spatula can smoothly perform waxing-up work without feeling any resistance.

Referring to FIG. 10(C), the front end of the nozzle member 7 is closed and a slot aperture 744 with a constant width and a constant length is provided close to the front end of the nozzle member 7 and on the external surface of the member in the longitudinal direction so that the melted wax can be delivered from the aperture 744.

Referring to FIG. 10(D), the closed surface of the tip 74 of the nozzle member 7, shown in FIG. 10(C), is modified to a curved surface 745 which is curved inward. This curved surface 745 is best suited as a spatula tip for final curve finish. These tip shapes of the nozzle member are also applied to the nozzle tip of the first embodiment, except for the hollow needle-shaped adaptor 17. The needle-shaped adaptor 17 should be used only when the melted wax is delivered in a thin extruded form. Instead of the needle-shaped adaptor 17, an example of a cap-shaped adaptor which allow the melted wax to exude is shown in FIG. 11.

More specifically, this adaptor has a cap 35 comprising netted metal fiber made of copper or other metals with high conductivity. The adaptor is secured by a means for securing 36. By removing the means for securing 36, the adaptor 35 can be replaced. Due to this construction, the melted wax accumulated at the tip 74 of the nozzle member 7 exudes through the metal fiber of the adaptor 35 and is delivered externally. Since the metal fiber is elastic and has a netted form, the adaptor 35 can function as a brush tip. Therefore, this adaptor is best suited for the waxing-up work requiring multiple layers of thin wax.

While several preferred embodiments of the present invention has been described, it will be understood that various structural modifications such as addition, replacement and change may be made without departing from the spirit or scope of the following claims. For example, a pair of caterpillars can be used as a means of feeding wax so that the wax can be held and fed by the caterpillars. In this case, higher stability is obtained since the wax is placed on the lower caterpillar. In the case of the means for feeding wax using gears, a great force is required to directly drive the feed gears using a finger. To solve this problem, many gears can be combined by properly considering the gear ratio so that the wax can be fed with a smaller force. Furthermore, what is called an air gun or a means using a compression spring can also be used. Instead of the switch of the first embodiment, a foot controller can be used. A means for advancing the plunger by operating an electric motor is also possible. The solid wax can have a form of a hexagonal bar or other bar shapes. Moreover, this apparatus is also used for dipping. That is, dipping is possibly by permeating the melted wax delivered from the nozzle tip to a syringe for example and by damping a tooth abutment using the syringe. By this operation, a thin layer of wax can be applied to the required portions. As a result, excessively thick application is prevented and work efficiency is improved. Furthermore, this apparatus can also be used for handicraft.

As described above, the handy apparatus of the present invention can melt a required amount of wax at a required time. Consequently, all the defects caused by the conventional waxing-up method are completely eliminated.

I claim:

1. An apparatus for melting a bar of wax having a front face and directing a flow of the molten wax, the apparatus comprising:
    a casing which accommodates said bar of wax;
    a nozzle associated with the front of said casing and adapted to receive the flow of molten wax;
    a substantially flat heating plate disposed at the rear of said nozzle and positioned substantially parallel to said front face of said bar of wax, and;
    feed means for feeding said bar of wax against said heating plate,
    wherein said heating plate melts the front of said bar of wax so that the molten wax flows through said nozzle.

2. An apparatus as defined in claim 1, wherein said feed means comprises:
    a compressed air inlet member associated with the rear of said casing; and
    a plunger which is movably accommodated in said casing so that said plunger can be pushed forward by the pressure of compressed air.

3. An apparatus as defined in claim 1, further comprising:
    a ceramic heater for heating said heating plate, said heater comprising a ceramic body, an electrical resistor material on said ceramic body, and ceramic material insulatively covering said resistor material.

4. An apparatus as defined in claim 1, further comprising:
    a hollow connection member coupling said casing to said nozzle so that said heating plate disposed at the rear of said nozzle is located inside said hollow connection member; and
    heating means connected to said nozzle so that said nozzle transmits heat to said heating plate.

5. An apparatus as defined in claim 1, further comprising:
    a seal between said connection member and the surface of said bar of wax to prevent molten wax from flowing toward the back of said casing.

6. An apparatus as defined in claim 1, further comprising:
    a retaining sleeve coupled to said connection member and supporting said casing along the length of said casing.

7. An apparatus as defined in claim 1, further comprising:
    an ON/OFF switch for said feed means provided on said retaining sleeve; and
    an ON/OFF switch for said heating means provided outside the apparatus.

8. An apparatus as defined in claim 7, wherein said ON/OFF switch for said feed means is a foot control switch.

9. An apparatus as defined in claim 3, wherein said ceramic heater is coupled around said nozzle member.

10. An apparatus as defined in claim 1, wherein said bar of wax is cylindrical.

11. An apparatus as defined in claim 1, wherein the front of said nozzle has an oblique opening.

12. An apparatus as defined in claim 1, wherein the front of said nozzle is closed and a slot aperture is provided on the side of said nozzle.

13. An apparatus as defined in claim 12, wherein said closed front of said nozzle is inwardly curved.

14. An apparatus as defined in claim 1, further comprising:
    a hollow needle-shaped member at the front of said nozzle for directing the flow of the molten wax.

15. An apparatus as defined in claim 1, further comprising:
    a cap having a plurality of metal fibers disposed over the front of said nozzle which allows wax from the nozzle to extrude through the metal fibers.

16. An apparatus as defined in claim 1, wherein the rear of said nozzle is flanged to form said heating plate.

* * * * *